United States Patent [19]

Anderson et al.

[11] 4,288,355

[45] Sep. 8, 1981

[54] SURGICAL CEMENT COMPOSITION

[75] Inventors: Harvey L. Anderson, Dellwood; Ronald M. Randklev, White Bear Lake, both of Minn.

[73] Assignee: Minnesota Mining and Manufacturing Company, St. Paul, Minn.

[21] Appl. No.: 908,576

[22] Filed: May 22, 1978

[51] Int. Cl.³ ............................................. C08K 3/22
[52] U.S. Cl. ........................... 260/29.6 M; 260/42.55
[58] Field of Search .......... 260/29.6 M, 42.55, 29.6 H

[56] References Cited

U.S. PATENT DOCUMENTS

| | | | |
|---|---|---|---|
| 2,760,431 | 8/1956 | Beatty | 260/29.6 M |
| 3,655,605 | 4/1972 | Smith | 260/29.6 M |
| 3,741,926 | 6/1973 | Jurecic | 260/29.6 M |
| 3,804,794 | 4/1974 | Schmitt | 260/29.6 M |
| 3,962,267 | 6/1976 | Suzuki | 260/29.6 M |
| 4,016,124 | 4/1977 | Crisp | 260/29.6 M |

*Primary Examiner*—Paul R. Michl
*Attorney, Agent, or Firm*—C. Alexander; D. M. Sell; D. P. Edmundson

[57] ABSTRACT

A surgical cement comprised of a concentrated non-gelling aqueous solution of a polycarboxylic acid and an aqueous suspension of metal oxide powder which when mixed together form a plastic mass which is formable into the desired shape before it hardens. The surgical cement has particular utility for dental applications.

10 Claims, No Drawings

SURGICAL CEMENT COMPOSITION

BACKGROUND OF THE INVENTION

This invention relates to two-part surgical cements. More particularly, the invention relates to surgical cements useful in dentistry.

Surgical cements used in dentistry are generally composed of a powder and a liquid which, when mixed together, react to form a workable plastic mass which subsequently hardens to a coherent cement. The cement is useful in producing a solid union between two surfaces (for example, to retain metallic and non-metallic castings in a prepared tooth, or to adhere crowns, bridges and orthodontic appliances to the tooth). Depending upon the chemical composition of the surgical cement it may also be used as a cavity liner or base, as a temporary tooth restoration, as a root canal filling, or for pulp capping. The primary requisites for a dental cement are adequate strength, adhesion to the tooth, resistance to erosion in oral fluid, and a low level of irritancy to tooth pulp.

Early surgical cements used in dentistry were composed of lime and concentrated phosphoric acid and were characterized by a number of disadvantages. For example, they were highly irritating and injurious to tooth pulp and they were also very soluble in oral fluid. Later zinc oxide, and then calcined zinc oxide, were substituted for the lime. This resulted in improved compressive strength but the cement still suffered from poor adhesion to the tooth and was also irritating to the pulp.

Another widely used dental cement was based on zinc oxide-eugenol combinations which were not harmful to the pulp. However, such compositions had very low compressive strength and were not resistant to abrasion.

A more recent dental cement is a polycarboxylate cement of the type described in U.S. Pat. Nos. 3,655,605; 3,751,391; 3,804,794 and 3,814,717; and British Pat. No. 1,139,430. This type of dental cement has exhibited good adhesion to the tooth surface and is quite insoluble when cured.

In attempts to improve the compressive strength of the polycarboxylate dental cements, copolymerized carboxylic acids were utilized, e.g., as described in U.S. Pat. Nos. 3,804,794; 3,882,080; 3,962,267 and 4,016,124. In spite of the use of a copolymer, the inherent disadvantages of a polycarboxylate cement, i.e., low compressive strength and mixing difficulty, still remained.

Typically the polycarboxylate component of previously described cements is in the form of a liquid (although it may be in the form of a powder) which must be mixed thoroughly with the powder component (e.g., metal oxide) at the time of use to form a creamy paste. This creamy paste is then placed into the crown or bridge appliance which is then applied to the prepared site in the mouth. The paste is permitted to harden and excess material is removed. However, it is difficult to thoroughly and quickly mix the powder compoent and the liquid component. Furthermore, the dental cement begins to harden within 1.5-2.5 minutes and is completely set within about 8 minutes. Although various techniques may be used to incorporate the powder into the mixture in increments, the required mixing time is still somewhat prolonged. As a result, the dentist's working time with the dental cement is seriously shortened. Some have suggested that the two components be mixed on a chilled glass slab in order to slow the reaction, but if the chilled slab is below the dew point there can be condensation of moisture thereon to introduce even further problems. Moreover, because of the necessary haste in mixing the two components they are seldom proportioned accurately for optimum results.

The present invention overcomes the common deficiencies inherent in the two-component (liquid and powder) dental cement compositions.

SUMMARY OF THE INVENTION

In accordance with the present invention there is provided a surgical cement which is comprised of a mixture of (a) an aqueous suspension of a metal oxide powder and (b) an aqueous solution of polycarboxylic acid, in a weight ratio of about 0.5:1 to about 8:1. The metal oxide powder makes up about 30 to 60 percent by volume of the suspension, and the acid in the acid component is present in the solution at about 55 to 80 percent of the total solution weight.

The two parts or components can be readily quickly and simply mixed without use of special equipment or procedures. Since the metal oxide particles are already dispersed in an aqueous medium there is no need to break up powder agglomerates as is commonly the case with prior art cements having separate liquid and powder components.

It is surprising that the metal oxide powder, when made into a paste with water, would function properly in a dental cement. It would be expected that pre-dispersion of the metal oxide powder in water (which maximizes the metal oxide and hydroxide ions available for later reaction with polycarboxylic acid) would greatly accelerate the cure rate of the surgical cement when the two pastes are mixed. However, it has been found that there is surprisingly little change in the rate of reaction of the metal oxide and the acid when packaged in accordance with the present invention. In fact, the cements of this invention have exhibited slightly longer working times than previously observed. This increased working time is of great advantage to the dentist.

It is even more surprising that the cement provided herein does not exhibit a reduction in compressive strength when cured. It would be expected that the use of a low molecular weight solution of polycarboxylic acid would cause a reduction of compressive strength of the cured cement. However it has been found that the cement of the present invention exhibits high compressive strengths even when low molecular weight polycarboxylic acids are used.

DETAILED DESCRIPTION OF THE INVENTION

A surgical cement in accordance with the present invention utilizes, as one component, a paste comprising an aqueous suspension of polyvalent metal oxide powder. Preferably, the metal oxide powder may be one or more of the following: zinc oxide, calcium oxide, magnesium oxide, aluminum oxide, aluminosilicate glasses (such as are described in U.S. Pat. No. 3,814,717) and other polyvalent-cation-containing glasses known in the art or other well-known metal oxides which are surgically acceptable and which will react with the polycarboxylic acid to form a hardened cement. Deactivation of the metal oxide or mixtures of metal oxides by heating is frequently desirable to allow sufficient working time of the cement. Particularly preferred are mixtures of magnesium and zinc oxides which are calcined by heating at temperatures up to 1300° C. for a period of at least 20 hours or more and then ground to a powder of less than about 15 microns particle size. This paste generally comprises 30 to 60 percent by volume of metal oxide in water. Above 60 percent by volume of metal oxide, the paste is normally too thick to easily dispense and mix.

The metal oxide powder paste is prepared by mixing the powder with the water. A variety of mixing means are suitable and is described hereinafter. To improve the handling properties of the paste as well as to prevent settling of the powder, various conventional additives (thickeners) may be used. For example, 4.5 parts of colloidal bentonite can be added to 95.5 parts of water and this mixture can then be used as a vehicle for the powder. The resultant paste is stable to settling and flows freely from the tube or syringe. Other useful water soluble resins and gums are hydroxypropylguar, methyl cellulose and carboxymethylhydroxypropylguar, which is most preferred.

It has been found advantageous to add sorbitol, glycerol or other humectants to the water vehicle to retard the tendency for this paste to dry out in storage. Many of these materials also contribute desirable handling characteristics to the paste.

It has also been found that bacteriostatic agents can be added to the pastes, if desired, to control bacterial contamination. For example 200 parts per million of sodium hypochlorite or 400 parts per million of a mixture of methyl and propylesters of p-hydroxybenzoic acid have been found to be effective. Stannous fluoride has also been found to be an effective bacteriostatic agent and offers the additional advantage of preventing tooth decay once the cement is in place.

It is surprising that many of these additives have no deleterious effect on the cement; thus a wide choice of compounding ingredients commonly used in the cosmetic art can be used.

Other materials can be added to the metal oxide powder to achieve characteristics suitable for specialized applications. For example, increased radiopacity can be achieved by adding barium sulfate powder to the metal oxide powder before making the second paste. A mixture of 75 parts of barium sulfate and 25 parts of zinc oxide is particularly useful in an endodontic cement, having adequate radiopacity and extended working time. It is contemplated that further modification in the formulation can be made by the addition of other metal oxides or metal hydroxides of such polyvalent metals as calcium, copper, barium, strontium, cadmium, cobalt and nickel.

It has been found that larger percentages of water vehicle (i.e., water plus thickeners and other soluble additives) in the paste provide for easier mixing but cause an undesired drop of compressive strength of the cured cement. A preferred range for water content is about 10-30 percent by weight if the metal oxide powder is predominantly zinc oxide, with the most preferred being 15 percent by weight of the total paste. For other metal oxide powders, the range is about 30 to about 60 percent by volume of powder due to the different densities.

The method of preparation of the oxide paste has a direct influence on its stability. First the thickener and other soluble additives are added to water and mixed with moderate stirring action until the thickener is completely dissolved. The oxide powder is then added and the paste is mixed using a moderate speed shear mixer, e.g., a paint shaker moving at approximately 710 cycles per minute (Model No. 5110, Red Deveil, Inc.). It has been found that mixing at too high a shear (e.g., in a Waring blender) causes scission of the hydrated thickener molecules which causes a reduction in the viscosity imparted by the thickener, and too low a shear results in the water exuding from the formed paste during storage.

The particle size of the metal oxide powder can be varied over a broad range depending upon the application for the cement and the metal oxide being used. It has been found that a superior paste having optimal curing time is provided by blending a minor fraction of recalcined and milled oxide, which has been milled to a finer particle size, with a major fraction of the coarser recalcined and milled oxide. This blend increases the ease of mixing of the powdered oxides.

In the preferred metal oxide paste the calcined zinc oxide-magnesium oxide is milled to obtain a coarse mean particle size of approximately 4 microns, and a portion thereof is then further ballmilled for an additional 8 hours to obtain finer particles. The preferred paste then consists of 50% by weight coarse particles, 35% by weight fine particles and 15% aqueous vehicle.

The surgical cement of the present invention is further comprised of an aqueous solution of polycarboxylic acid. Typically the acid of the prior art is about 30 to about 60 percent by weight of the solution. At concentrations of acid above 55 percent gelation often occurs during storage which renders the mixing of the cement extremely difficult. It has now been found that very low molecular weight polycarboxylic acid can be concentrated and surprisingly will not gel and will produce a cement of sufficient compressive strength and a slower cure. This is surprising because it would be generally expected that the cement's compressive strength would drop rapidly with the decrease in the molecular weight of the polycarboxylic acid.

The polycarboxylic acid may be of any type. Preferably the polycarboxylic acid is selected from the group consisting of polyacrylic acid, polymers of unsaturated alpha, beta-dicarboxylic acids, methacrylic acid, and copolymers of acrylic acid and unsaturated alpha, beta-dicarboxylic acids. Copolymers of acrylic acid or of the unsaturated $\alpha,\beta$ dicarboxylic acids with other monomers such as acrylamide, acrylonitrile, methacrylic acid, and N-vinyl pyrrolidone may also be used as well as mixtures of these polymers and copolymers. Particularly preferred is polyacrylic acid.

The number average molecular weight of the polycarboxylic acid should generally be in the range of about 2,000 to 20,000, and the acid should be concentrated in water solution in the range of 55 to 80 weight percent to form a paste.

As an example a typical polyacrylic paste would be made by taking a commercially available polyacrylic acid such as "Goodrite K-732" manufactured by B. F. Goodrich Co. having a concentration of 47% solids and a molecular weight of 5000, and concentrating it further by rotating vacuum flask under suction for two hours in a heated mineral oil bath whose temperature is gradually increased to 90° C. Upon cooling the polyacid takes a paste form without further additives and has a solids concentration in the range of about 70-75%. This highly concentrated polyacid solution has been found stable and not subject to gelation over extended periods of storage.

A polyacid paste which exhibits a faster curing time may be made by blending the low molecular weight polycarboxylic acid with a higher weight polycarboxylic acid. The blend preferably contains a substantial percentage, about 60–85 percent, of low molecular weight polyacid (i.e., having a number average molecular weight in the range of about 2000 to 20,000) and minor percentage, about 15 to 40 percent, of a higher molecular weight polyacid. The preferred blend is concentrated to about 60 to 70% solids in water.

It is surprising that the blend which contains the higher molecular weight polyacid does not exhibit gelation during storage as does a paste of the same high molecular weight polyacid alone in paste form. There is also evidence of synergism in that cement made with this mixture has higher compressive strength than would be expected from the contributions of the two molecular weight polyacids used individually.

The advantages of the present invention may be better seen by the following nonlimiting examples in which all parts are parts by weight of the paste:

EXAMPLE 1

A two-part paste surgical cement is prepared. The first paste is prepared by blending the following materials:

| | |
|---|---|
| calcined zinc-oxide-magnesium oxide powder | 80.75 parts |
| U.S.P. 12 uncalcined zinc oxide | 4.25 parts |
| Boiled water | 13.8435 parts |
| Vee-Gum H.V. (colloidal bentonite) | 0.675 parts |
| Glycerol | .45 parts |
| m-paraben (methyl p-hydroxybenzoate) | .027 parts |
| p-paraben (propyl p-hydroxybenzoate) | .0045 parts |

The first paste is prepared by blending 97 parts by weight zinc oxide ("U.S.P. 12," New Jersey Zinc Co.) and 7.15 parts by weight magnesium carbonate ("Magcarb L," Merck and Co.)., followed by calcination according to the methods of U.S. Pat. No. 3,655,605, incorporated herein by reference. After calcination the material comprised 97 percent by weight zinc oxide and 3 percent magnesium oxide. The material was then crushed in a ball mill to 300–400 mesh fineness. The calcined zinc oxide-magnesium oxide powder was re-calcined and milled for an additional 3.5 hours to an average particle size of 4 microns to which is added 0.04 parts by weight zinc stearate and then ball milled for 30 min. The resulting powder is sometimes hereinafter referred to as #1905 zinc oxide. This mixture is then mixed with the uncalcined zinc oxide ("U.S.P. 12" New Jersey Zinc Co.). This zinc oxide mixture is added to the water which was previously mixed at moderate speed with 0.675 part colloidal bentonite ("Vee Gum HV," R. T. Vanderbilt Co.), 0.45 part glycerol, 0.27 part m-paraben and 0.0045 part p-paraben. The resulting mixture is placed on a paint shaker until the complete mixture produces a smooth paste.

A second paste was prepared by concentrating an aqueous solution of polyacrylic acid ("Goodrite K-732" manufacturd by B. F. Goodrich Co.; molecular weight of 5000) utilizing a rotating vacuum flask under suction for two hours in a heated mineral oil bath whose temperature is gradually increased to 90° C.

Alliquots of the first and second pastes were combined and stirred to produce dental cements having desirable properties.

EXAMPLE 2

A two part paste surgical cement is prepared. The first paste is prepared using #1905 zinc oxide in a manner described in Example 1. Fifty-five parts of the zinc oxide are mixed with 30 parts uncalcined zinc oxide. This mixture is placed in 14.3685 parts boiled water to which has been previously mixed at a low speed with 0.15 parts carboxymethyl-hydroxypropylguar (Guar CMHP, Stein, Hall and Co.), 0.45 part sorbitol, 0.027 part m-paraben and 0.0045 part p-paraben. The mixture was stirred to a paste by the method of Example 1.

A second paste was prepared by blending 3 parts of a 70% by weight aqueous solution of 5000 molecular weight polyacrylic acid ("Goodrite K-732") with 1 part of a 46.5% by weight of a 40,000 molecular weight aqueous polyacrylic acid. The blend was concentrated by the method outlined in Example 1 to yield a concentration of about 65 to 75 percent solids.

The first paste (A) and second paste (B) are packed into appropriate lined collapsible tubes. Cements were prepared utilizing various ratios of A to B. A 2:1 mixture by weight of "A" and "B" pastes provided excellent handling properties with a set time of 11–12 minutes at ambient conditions which are excellent for placement of multiple unit crowns and bridges. The same components mixed at 2.5:1 weight ratio of "A" and "B" set in 8½ minutes at ambient conditions which is desirable for most placements. The combination pack thus provides ample set time latitude for most applications with excellent handling properties over the entire range.

Compressive strength of this cement mixed at a 2:1 ratio is from 9200–9500 psi (645–670 kg/cm$^2$) which is an improvement over the approximate average compression strength of 550 kg/cm$^2$ of commercially available zinc oxide powder/polyacrylic acid cements. Strength of the 2.5:1 mix is in excess of 8000 psi (565 kg/cm$^2$+). The paste components are easy to expel from the tubes and can be quickly mixed to a uniform consistency.

EXAMPLE 3

A metal oxide paste is formed by mixing 85 parts #1905 zinc oxide with 14.3685 parts boiled water to which has been previously mixed, in accordance with Example 1, 0.15 part Guar CMHP, 0.45 part sorbitol, 0.027 part m-paraben and 0.0045 part p-paraben.

A second paste of polyacrylic acid is made in accordance with Example 2.

Increments of the metal oxide paste A and the polyacrylic acid paste B were mixed in the ratio indicated in Table I and the compressive strengths were measured.

TABLE I

| MIX RATIO A:B By weight | COMPRESSION STRENGTH |
|---|---|
| 2:1 | 9000–9800 psi - (635–690 kg/cm$^2$) |
| 2.5:1 | 8000–8600 psi - (563–605 kg/cm$^2$) |
| 3:1 | 7000–7600 psi - (492–535 kg/cm$^2$) |

EXAMPLE 4

A two paste surgical cement is prepared. The first paste is prepared in accordance with Example 3 utilizing the following materials: 80 parts #1905 zinc oxide, 18.098 parts boiled water, 1.66 parts glycerol, 0.2 part hydroxypropylguar (Jaguar HP-11, Stein, Hall and Co.), 0.036 part m-paraben and 0.006 part p-paraben.

The second paste was made in accordance with the method outlined in Example 1 utilizing 87.33 parts "Goodrite 732" (molecular weight of 5000) polyacrylic acid, 9.70 parts tricalcium phosphate (Mallinkrodt, Inc.) and 2.92 parts colloidal silica (Cab-O-Sil M-5, Cabot Corp.). The above pastes were compounded and separately packed into lined collapsible tubes. These pastes are very satisfactory as endodontic cements, having satisfactory work time and handling properties.

Working time of the cement was greater than 24 minutes. Accordingly the cement is especially useful for root canal sealing where prolonged working time is required for insertion and placement of gutta percha points. The cement also has good fluidity which is required for penetrating into the narrow root canal. The set time of the cement is over one hour. The compressive strength of the cement is 1500–2000 psi (106–141 kg/cm$^2$).

EXAMPLE 5

A two paste surgical cement was prepared utilizing the following materials;

| Paste "A" | |
| --- | --- |
| #1905 zinc oxide | = 50.0 parts |
| U.S.P. - 12 uncalcined zinc oxide | = 16.68 |
| Boiled water | = 28.99 |
| Vee-Gum HV | = 1.50 |
| Glycerol | = 2.76 |
| m-paraben | = 0.06 |
| p-paraben | = 0.01 |
| Paste "B" | |
| 40,000 molecular weight polyacrylic acid (40% conc.) (60% water) | = 75 parts |
| tri calcium phosphate N.F. | = 25 |

The separate pastes were prepared as in Example No. 1. This cement was developed to serve as a base or lining under other cements. The handling properties of this cement appeared satisfactory.

EXAMPLE 6

A two paste surgical cement was prepared utilizing the following materials:

| Paste "A" | |
| --- | --- |
| Glass Ionomer Powder from Amalgamated Dental Products - England - distributed by Claudius Ash, Inc. - Niagara Falls, New York. (Described as prepared by fusing together a mixture of calcium, sodium and aluminum to form a calcium aluminium silicate glass and will be referred to herein as ASPA powder). | = 80.0 parts |
| Boiled water | = 19.158 parts |
| Guar CMHP | = 0.20 |
| Sorbitol | = 0.60 |
| m-paraben | = 0.036 |
| p-paraben | = 0.006 |
| Paste "B" | |
| "Goodrite K-732" - 5000 molecular weight polyacrylic acid (75% conc.) (25% water) | = 75 |
| 40,000 molecular weight polyacrylic acid (43% conc.) (57% water) | = 25 |

Both pastes A and B were prepared by the method of Example 1. While it was difficult to determine set time of the cements because of the rubbery state, the set time of the 2/1 mix of paste "A" and "B" of this Example appeared to have a set time of over 20 minutes.

This cement, similar to those of U.S. Pat. Nos. 3,814,717—Wilson and 4,016,124—Crisp tends to cure to a more elastic cement than those using zinc oxide. Because of this rubbery consistency, these cements are not as useful for bonding bridges, caps and the like but are more useful as filling materials or as surgical cements.

EXAMPLE 7

A further polyacid paste was formulated in accordance with Example 1, using 40,000 molecular weight polyacrylic acid at a concentration of 52% in water. When this polyacid paste was mixed with the powder paste "A" of Example 6, in a weight ratio of 2 parts paste "A" to 1 part paste "B," the set time was about 12 minutes, comparable to that of the cement of Example 6 while the mixing time was only 10 seconds.

When the polyacid paste of this Example was mixed in a 1 to 3 ratio by weight with the powder paste of Example 6, set time was speeded to about 7–8 minutes. This indicates that various ratios of Paste "A" and Paste "B" or the polyacid paste of this Example can be mixed to provide various set-times.

It was found that fluoroaluminosilica glasses can be used to prepare pastes with the addition of thickened water, which pastes are useful in preparing cements similar in set-time and physical properties to those produced by the more traditional powder/liquid methods but being much easier and much faster to mix and therefore being more versatile to use.

EXAMPLE 8

A first paste of 5000 molecular weight polyacrylic acid made in accordance with Example 1 and mixed with a second paste made by the method outlined in Example 1 and comprised of a glass comprising 65:3 parts ZnO, 13.6 parts B$_2$O$_3$ and 16.1 parts SiO$_2$ in a 1.3/1 ratio of second paste to first paste. The setting time was found to be in the useful range.

EXAMPLE 9

A surgical cement was made in accordance with Example 8 wherein the second paste comprised a glass comprising 50.9 parts ZnO, 14.8 parts Al$_2$O$_3$ and 34.3 parts SiO$_2$. The pastes are mixed in a ratio of 1.3/1 (second to first).

The resulting cement exhibited a useful setting time.

What is claimed is:

1. A process for the preparation of a surgical cement which comprises forming a mixture of an aqueous suspension of metal oxide powder, said powder being about 30 to 60 percent by volume of said suspension, and an aqueous solution of polycarboxylic acid, said acid being about 55 to about 80 percent by weight of said solution, and wherein the weight ratio of said suspension of metal oxide powder to said aqueous polycarboxylic acid is 0.5/1 to 8/1.

2. A process in accordance with claim 1 wherein said metal oxide powder comprises zinc oxide.

3. A process in accordance with claim 1 wherein the metal oxide powder comprises polyvalent-cation-containing glass.

4. A process in accordance with claim 1, wherein said polycarboxylic acid is selected from the group consisting of polyacrylic acid, polymethacrylic acid, polymers derived from unsaturated alpha, beta-dicarboxylic acids, and copolymers of acrylic acid, methacrylic acid and unsaturated alpha, beta-dicarboxylic acids.

5. A process in accordance with claim 1, wherein said polycarboxylic acid comprises polyacrylic acid.

6. A process in accordance with claim 5 wherein said polyacrylic acid has a molecular weight of about 2000 to about 20,000.

7. A process in accordance with claim 1 wherein said polycarboxylic acid comprises a blend of a first polyacrylic acid having molecular weight of about 2,000 to about 20,000 and a second polyacrylic acid having a molecular weight greater than about 20,000 and wherein said first acid is present in an amount greater than said second acid.

8. A process in accordance with claim 1 wherein said aqueous solution of polycarboxylic acid also contains a thickener.

9. A process in accordance with claim 1 wherein said aqueous solution of polycarboxylic and said suspension of metal oxide powder are in paste form and are dispensed from a syringe.

10. A surgical cement pack comprising (a) a first paste consisting essentially of an aqueous solution of polycarboxylic acid, said acid being about 55 to 80 percent by weight of said solution, and (b) a second paste consisting essentially of an aqueous suspension of metal oxide powder, said powder being about 30 to 60 percent by volume of said suspension; said pack having means to prevent premature reaction between said first and second pastes; whereby when said second paste is mixed with said first paste, in a weight ratio of about 0.5/1 to 8/1, a plastic mass is formed which rapidly hardens as a surgical cement but which remains plastic for a time sufficient to permit forming thereof into the desired shape.

* * * * *

UNITED STATES PATENT AND TRADEMARK OFFICE
CERTIFICATE OF CORRECTION

PATENT NO. : 4,288,355
DATED : September 8, 1981
INVENTOR(S) : Harvey L. Anderson and Ronald M. Randklev It is certified that error appears in the above—identified patent and that said Letters Patent is hereby corrected as shown below:

Column 10, line 7, insert the word -- acid -- after "polycarboxylic".

Signed and Sealed this

Twenty-first Day of February 1984

[SEAL]

Attest:

Attesting Officer

GERALD J. MOSSINGHOFF

Commissioner of Patents and Trademarks